(12) United States Patent
Daum (10) Patent No.: US 10,736,599 B2
(45) Date of Patent: *Aug. 11, 2020

(54) CT SYSTEM AND METHOD FOR DETERMINING THE POSITION AND RANGE OF A MOBILE CONTROL ELEMENT FOR CONTROL OF THE CT SYSTEM

(71) Applicant: Siemens Aktiengesellschaft, Munich (DE)

(72) Inventor: Arnulf Daum, Bayreuth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/250,605

(22) Filed: Jan. 17, 2019

(65) Prior Publication Data
US 2019/0150873 A1    May 23, 2019

Related U.S. Application Data

(63) Continuation of application No. 15/078,339, filed on Mar. 23, 2016, now Pat. No. 10,182,785.

(30) Foreign Application Priority Data

Apr. 8, 2015 (DE) ......................... 10 2015 206 230

(51) Int. Cl.
*A61B 6/00* (2006.01)
*A61B 6/03* (2006.01)
(Continued)

(52) U.S. Cl.
CPC .............. *A61B 6/547* (2013.01); *A61B 6/032* (2013.01); *A61B 6/10* (2013.01); *A61B 6/548* (2013.01); *A61B 6/0407* (2013.01)

(58) Field of Classification Search
None
See application file for complete search history.

(56) References Cited

U.S. PATENT DOCUMENTS

| 2006/0244627 A1 | 11/2006 | Kagermeier et al. |
| 2008/0266085 A1 | 10/2008 | Kagermeier et al. |

(Continued)

FOREIGN PATENT DOCUMENTS

| CN | 1953702 | 4/2007 |
| CN | 101095180 | 12/2007 |

(Continued)

OTHER PUBLICATIONS

"www.pepperl-fuchs.de/global/en/23466.htm", Jan. 30, 2015.
(Continued)

*Primary Examiner* — Hoon K Song
(74) *Attorney, Agent, or Firm* — Harness, Dickey & Pierce, P.L.C.

(57) ABSTRACT

A CT system for a computed tomography examination is disclosed. In an embodiment, the CT system includes at least one mobile control element for control of the CT system, wirelessly connected to the CT system. At least one position and range determination facility is provided to determine the current position of the at least one control element in a range around the CT system. Furthermore, a method is disclosed for the position and range determination of a mobile control element for control of a CT system. A control and computing unit of a CT system are also disclosed.

24 Claims, 2 Drawing Sheets

(51) Int. Cl.
*A61B 6/10* (2006.01)
*A61B 6/04* (2006.01)

(56) References Cited

U.S. PATENT DOCUMENTS

| | | | |
|---|---|---|---|
| 2009/0069640 | A1 | 3/2009 | Rietzel et al. |
| 2011/0044519 | A1 | 2/2011 | Levasseur, Jr. et al. |
| 2012/0018641 | A1* | 1/2012 | Watanabe ............ A61B 6/4233 250/354.1 |

FOREIGN PATENT DOCUMENTS

| | | |
|---|---|---|
| DE | 10336731 | 3/2005 |
| DE | 102007019529 | 1/2009 |
| DE | 102007042337 | 3/2009 |
| DE | 102008018266 | 10/2009 |
| EP | 1479964 | 11/2004 |
| WO | WO-2005110208 | 11/2005 |

OTHER PUBLICATIONS

"www.pepperl-fuchs.de/global/en/23500.htm", Mar. 24, 2016.
German Office Action dated Feb. 11, 2016.
"iBeacon", in: en.wikipedia.org/wiki/IBeacon; 2014.
First Office Action dated Jun. 22, 2018 in Chinese Application No. 201602046193.
Non-Final Office Action dated Mar. 26, 2018 in U.S. Appl. No. 15/078,339.
Notice of Allowance dated Sep. 10, 2018 in U.S. Appl. No. 15/078,339.
Second Office Action dated Mar. 11, 2019 in Chinese Application No. 201610204 6193.
Office Action dated Oct. 23, 2019 in Chinese Application No. 201610204 6193.

* cited by examiner

FIG 2

CT SYSTEM AND METHOD FOR DETERMINING THE POSITION AND RANGE OF A MOBILE CONTROL ELEMENT FOR CONTROL OF THE CT SYSTEM

CROSS-REFERENCE TO RELATED APPLICATIONS

This application is a continuation of U.S. patent application Ser. No. 15/078,339, filed on Mar. 23, 2016, which claims priority under 35 U.S.C. § 119 to German patent application number DE 102015206230.9 filed Apr. 8, 2015, the entire contents of each of which are hereby incorporated herein by reference.

FIELD

At least one embodiment of the invention generally relates to a CT system for a computed tomography examination, at least having at least one mobile control element for control of the CT system, which is wirelessly connected to the CT system.

At least one embodiment of the invention further generally relates to a method for determining the position and range of a mobile control element for control of the CT system, wherein the control element is wirelessly connected to the CT system, and to a control and computing unit of the CT system.

BACKGROUND

Control of CT systems using mobile control elements is basically already known. There are a few safety regulations here, such as for instance the rapid accessibility to an emergency shutdown switch of the CT system. This requires a location monitoring of the control element or the specification of a fixed position, from which the CT system can be operated via the control element.

Simple mechanical encodings were hitherto used on the control element for this purpose. In other words, for instance, as soon as the control element is positioned in a fixed-location support, certain operating and control functions are activated. A location-independent and flexible control of the CT system is however not possible here.

SUMMARY

At least one embodiment of the invention provides a CT system with a flexible and location-independent control by adhering to the safety regulations.

Advantageous developments of the invention form the subject matter of the claims.

The inventor has recognized that a contactless determination of the position and range, in other words in general a location monitoring of a mobile control element, which is wirelessly connected to the CT system, allows for control of the CT system to be restricted to a certain predefined range around the CT system, so that the safety regulations, such as for instance the accessibility of the emergency shutdown switch or, that a positioning of the patient on a couch is only possible under visual control of the user, are adhered to.

For the sake of simplicity, conventional methods can be used for location monitoring of the control element. Here a two or three-dimensional range around the CT system can be predetermined and monitored to determine whether the control element is located inside or outside of the range. It is also possible to monitor a precise position of the control element and thus the distance from the CT system, wherein the predetermined distance in turn predefines the radius of a three-dimensional range. To ensure a redundant location monitoring, both the precise position of the control element and also a predetermined range can be determined and monitored. A range around the CT system can generally be defined for instance as a range, or in particular a range around the emergency shutdown switch or around the couch, in particular around the patient positioned on the couch.

If the control element is located outside of the range or it exceeds a predetermined distance, control of the CT system can be blocked, in particular certain safety-relevant components of the CT system, for instance a movement of the patient couch or the emission of x-ray radiation, can be shut down. Control of the CT system, in particular safety-relevant components, is then consequently only possible within the range or up to a certain distance.

Accordingly, in at least one embodiment the inventor proposes to improve a CT system for a computed tomography examination, in particular of a patient, at least having at least one mobile control element for control of the CT system, which is wirelessly connected to the CT system, accordingly such that at least one position and range determination facility is provided to determine the current position of the at least one control element in a predetermined range around the CT system. The CT system can, in accordance with at least one embodiment of the invention, only be controlled with the wireless control element in a predetermined range or up to a predetermined maximum distance, which in turn defines a circle radius and thus a range around the CT system. This allows for a significantly more flexible and location-independent operation than with known systems. The safety regulations for operation of the CT system are adhered to here. Moreover, the range and/or the distance can be individually predetermined and adjusted to the spatial conditions of the examination room.

Moreover, in an embodiment the inventors propose a method of position and range determination of a mobile control element for control of an afore-described, inventive CT system, wherein the control element is wirelessly connected to the CT system, at least having the steps: predetermine a range around the CT system, in which control of the CT system is enabled, determine a position of the control element and enable the control element provided the control element is in the predetermined range around the CT system. In return, control of the CT system is blocked by the control element in accordance with the invention if the control element is located outside of the predetermined range.

Moreover, at least one embodiment of the invention relates to a control and computing unit of a previously described, inventive CT system, upon which a program or program codes is/are stored, which during operation executes the afore-described inventive method.

Accordingly, in at least one embodiment the inventor proposes to improve a CT system for a computed tomography examination, in particular of a patient, at least having at least one mobile control element for control of the CT system, which is wirelessly connected to the CT system, accordingly such that at least one position and range determination facility is provided to determine the current position of the at least one control element in a predetermined range around the CT system. The CT system can, in accordance with at least one embodiment of the invention, only be controlled with the wireless control element in a predetermined range or up to a predetermined maximum distance, which in turn defines a circle radius and thus a range around the CT system. This allows for a significantly more flexible and location-independent operation than with known systems. The safety regulations for operation of the CT system are adhered to here. Moreover, the range and/or the distance can be individually predetermined and adjusted to the spatial conditions of the examination room.

One embodiment provides that the predetermined range is embodied around an emergency shutdown switch of the CT system. The safety regulations in respect of the rapid accessibility of the emergency shutdown switch during operation of the CT system with the mobile control element are adhered to here. During control of the CT system, the user is always located inside of the predetermined range, since otherwise mobile control is blocked.

A further embodiment provides that the predetermined range is embodied around a couch of the CT system, in particular around a patient positioned on the couch. This ensures that control of the movement of the couch for positioning the patient in the CT system is only possible if the user is located in the visual range of the couch or of the patient. It is thus possible to monitor that the control element does not fail to meet a predetermined distance from the patient. Therefore a close range around the patient or the couch, in which control is not possible, can thus be predetermined. This is advantageous above all in patients with cardiac pacemakers, since the signals sent by the control element can interfere with the performance of the cardiac pacemaker.

Moreover, in general certain ranges in the examination room can be predetermined, from which control with the control element is to be blocked. An operation can also be blocked for instance in the afore-described embodiment if the user has placed the control element on the couch in order for instance to align the patient on the couch or otherwise.

There are various embodiments for the at least one position and range determination facility, in brief location monitoring. Two or more position and range determination facilities can be used for a redundant monitoring. On the one hand a facility for determining the current position of the control element, in other words a tangible distance and on the other hand a facility for range determination, in other words for monitoring is preferably used to determine whether the control element is located inside or outside of a range. The predetermined and monitored range can be defined either two or three-dimensionally in the examination room of the CT system.

In one embodiment, the at least one position and range determination facility comprises at least one induction loop in order to define the predetermined range. The induction loop defines a two-dimensional range around the CT system, for instance around the emergency shutdown switch or the couch. This allows for monitoring of whether the control element is disposed inside or outside of the loop or of the range. It is also possible to lay a first induction loop around the couch so that control cannot occur too close to the patient, in order for instance not to interfere with a cardiac pacemaker and to lay a further induction loop around the CT system in order to predetermine a maximum range, outside of which operation is blocked.

In another embodiment, the at least one position and range determination facility comprises at least one camera, in order to determine the position of the at least one control element. The control element advantageously has at least one optical marker, which can be detected by the camera for position determination.

Another embodiment provides that the at least one position and range determination facility comprises at least one navigation facility for navigation in closed rooms, in order to determine the position of the at least one control element. This is preferably a navigation system such as iBeacon® by Apple. This navigation system operates with a number of transmitters, which are arranged distributed across the examination room of the CT system, and a receiver on the control element. The transmitters emit signals at regular time intervals, preferably radio signals, which are detected by the receiver. Here both the distance of the control element from the CT system can be determined and also a range around the CT system. The more transmitters are used, the more precise the location determination. With the aid of at least three transmitters, a two-dimensional location determination can advantageously take place. A three-dimensional location determination can advantageously take place with the aid of at least four transmitters.

According to another embodiment, the at least one position and range determination facility comprises at least one transmitter-receiver combination, in order to determine the position of the at least one control element according to the pulse range method. The transmitter is advantageously embodied as a light source, which emits light signals. The light signal can be reflected onto the control element and advantageously detected at a receiver. The distance from the control element can be determined on the basis of the transmit and receive time instant.

In another further embodiment, the at least one position and range determination facility comprises at least one GPS, in order to determine the position of the at least one control element. Both a three-dimensional range and also a tangible distance thereto can also be monitored here. The GPS is preferably embodied as a DPGS, in order to achieve greater accuracy in terms of position determination.

The at least one control element can be embodied for instance as part of a movable trolley or as a tablet PC.

Moreover, in an embodiment the inventors propose a method of position and range determination of a mobile control element for control of an afore-described, inventive CT system, wherein the control element is wirelessly connected to the CT system, at least having the steps: predetermine a range around the CT system, in which control of the CT system is enabled, determine a position of the control element and enable the control element provided the control element is in the predetermined range around the CT system. In return, control of the CT system is blocked by the control element in accordance with the invention if the control element is located outside of the predetermined range.

The safety regulations such as accessibility of the emergency shutdown switch on the CT system or couch controller can advantageously only be adhered to with the inventive method if the patient is located in the visual range of the user. This is of particular importance during the operation of components of the CT system which are relevant to safety and are a danger to individuals, for instance a movement of the patient couch or the emission of x-ray radiation.

A movement of a couch of the CT system is preferably stopped if the control element is located outside of the predetermined range, in other words the user is no longer in the visual range of the couch for instance. Emission of x-ray radiation from an emitter-detector system of the CT system is further preferably stopped if the control element is located outside of the predetermined range. The same advantageously applies if a predetermined distance between the CT system, in particular the couch or the emergency shutdown switch, and control element is exceeded.

Control and operation of the CT system, in particular of the safety-relevant components, is enabled by way of the method only in a predetermined range or up to a distance. To this end, the position of the control element is constantly monitored.

Moreover, at least one embodiment of the invention relates to a control and computing unit of a previously described, inventive CT system, upon which a program or program codes is/are stored, which during operation executes the afore-described inventive method.

The inventive CT system and the inventive method are further advantageous in that the afore-described position and range determination facilities can be used in an energy-saving manner so that these are particularly well suited to mobile, wireless control elements. Furthermore, the known position and range determination facilities are favorable and simple in terms of acquisition and maintenance. Both a navigation system by way of iBeacon® and also the pulse range method can be extended for bidirectional communication with the CT system.

BRIEF DESCRIPTION OF THE DRAWINGS

The invention is described in more detail on the basis of a preferred example embodiment with the aid of the figures, wherein only the features required to understand the invention are shown, in which in detail: 1: emergency shutdown switch; 2: mobile control element; 3: induction loop; B, B1, B2: range; C1: CT system; C2: first x-ray tube; C3: first detector; C4: second x-ray tube (optional); C5: second detector (optional); C6: gantry housing; C7: patient; C8: patient couch; C9: system axis; C10: control and computing unit; Prg1-Prgn: computer programs.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Further, although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

Figure 1:
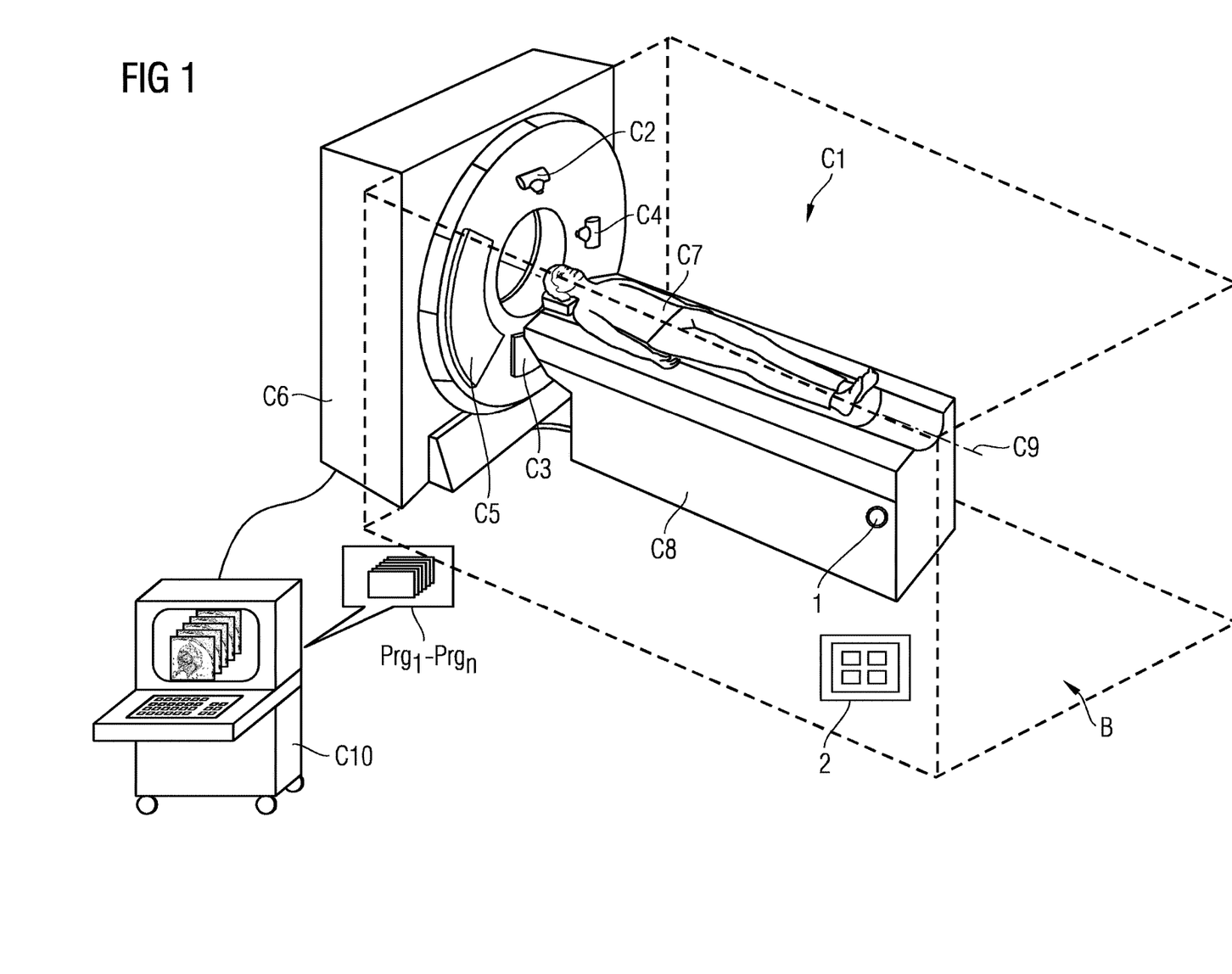
FIG. 1 shows a schematic representation of a CT system with a control and computing unit and a predetermined three-dimensional range around the emergency shutdown switch.

FIG. 1 shows an example CT system C1. The CT system C1 comprises a gantry housing C6, in which a gantry (not shown in more detail here) is disposed, to which a first x-ray tube C2 with an opposing first detector C3 is fastened. A second x-ray tube C4 with a second opposing detector C5 is optionally provided. A patient C7 is located on a patient couch C8 which can be moved in the direction of the system axis C9, with which, during the scanning with the x-ray radiation, he can be moved continuously or sequentially along the system axis C9 through a measurement field between the x-ray tubes C2 and C4 and the associated detectors C3 and C5 in each case. This process is controlled by a control and computing unit C10 with the aid of computer programs Prg1 to Prgn.

An emergency shutdown switch 1 is arranged on the couch C8. During operation and control of the CT system C1, for instance the movement of the couch C8, a user or a control element must be located in a predetermined range around the emergency shutdown switch 1 in order to adhere to existing safety regulations. An inventive position and range determination facility is provided here on the CT system C1.

With the position and range determination facility, a three-dimensional range around the emergency shutdown switch 1 is defined in the embodiment according to FIG. 1, in which operation of the CT system C1 with the mobile control element 2 is enabled. The control element 2 is embodied here as a tablet PC. The three-dimensional range is shown in FIG. 1 as a dashed cuboid. The range essentially extends around the couch C8. According to the embodiment shown here, the three-dimensional range is defined by a number of transmitters of the navigation system iBeacon®, which are arranged on the walls or the ceiling of the examination room for instance. A receiver of the iBeacon® navigation system is located in the mobile control element 2. As soon as the control element 2 leaves the range B, control of the couch C8 with the control element 2 is no longer possible.

Figure 2:
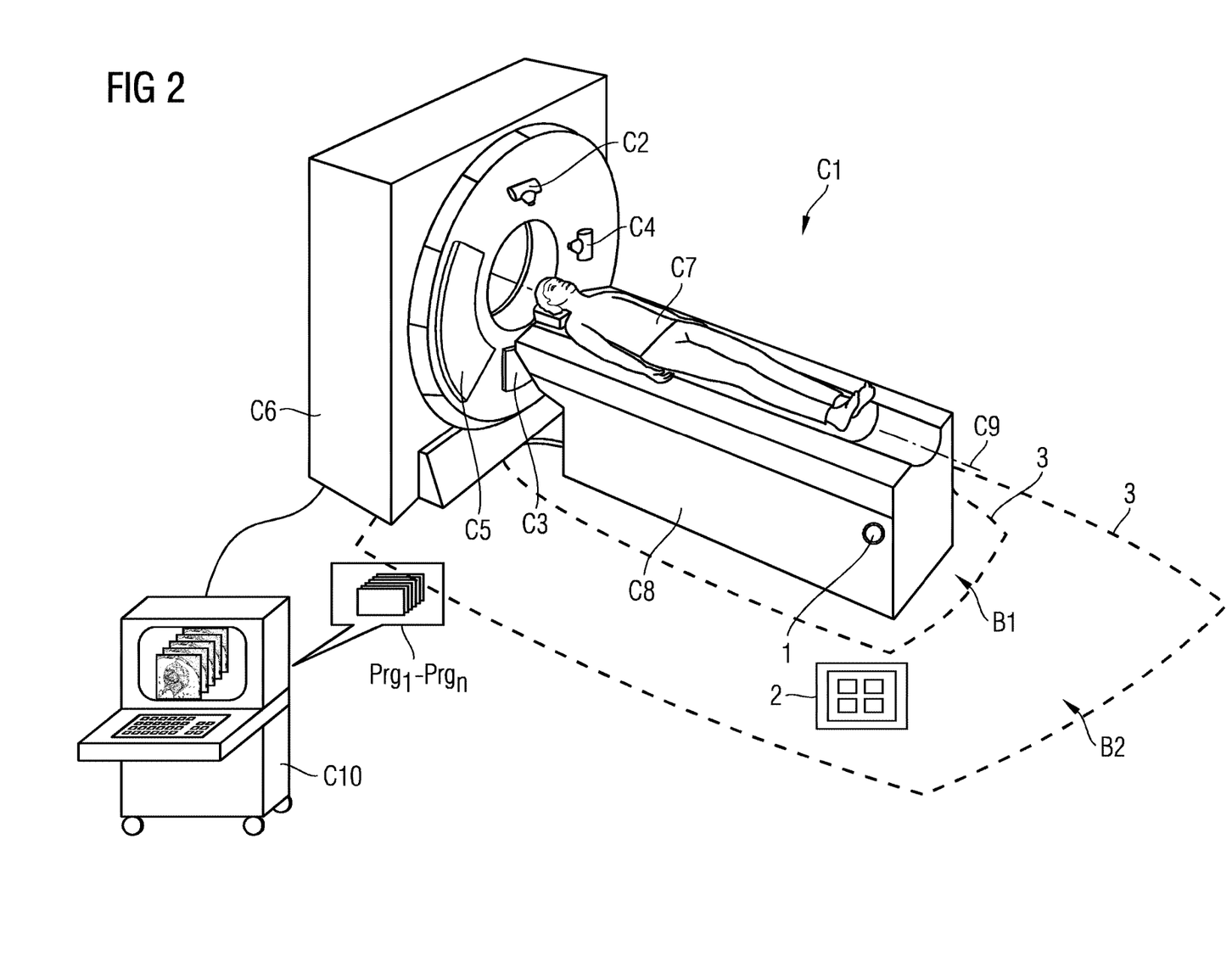
FIG. 2 shows a schematic representation of the CT system according to FIG. 1 and a predetermined two-dimensional range around the emergency shutdown switch.

FIG. 2 shows a further schematic representation of the CT system C1 according to FIG. 1. In this embodiment, a first two-dimensional range B1 around the couch C8 and a second two-dimensional range B2 around the emergency off switch 1 is defined. The ranges B1 and B2 are each defined by way of an induction loop 3, which is embedded in the floor of the examination room for instance. Control of the CT system C1 with the mobile control element 2 is only possible if the control element 2 is located between the two induction loops 3, in other words outside of the first range B1 or inside of the second range B2.

Although the invention has been illustrated and described in greater detail by the preferred example embodiment, the invention is not limited by the examples disclosed and the person skilled in the art will be able to derive other variations on this basis without departing from the scope of protection of the invention.

The aforementioned description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods. Further, elements and/or features of different example embodiments may be combined with each other and/or substituted for each other within the scope of this disclosure and appended claims.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Further, at least one embodiment of the invention relates to a non-transitory computer-readable storage medium comprising electronically readable control information stored thereon, configured in such that when the storage medium is used in a controller of a magnetic resonance device, at least one embodiment of the method is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An imaging modality comprising:
a memory storing computer-readable instructions; and
at least one processor coupled to the memory and configured to execute the computer-readable instructions to
determine whether a mobile control element configured to control the imaging modality is located greater than a first threshold distance away from the imaging modality, the imaging modality configured to communicate with the mobile control element via a wireless communication link, and the first threshold distance being shorter than a communication range of the wireless communication link, and
disable one or more functions of the imaging modality in response to determining that the mobile control element is located greater than the first threshold distance away from the imaging modality.

2. The imaging modality of claim 1, further comprising:
an emergency shutdown switch, wherein
the first threshold distance is measured from the emergency shutdown switch.

3. The imaging modality of claim 1, further comprising:
a couch, wherein
the first threshold distance is measured from the couch.

4. The imaging modality of claim 1, further comprising:
at least one induction loop defining the first threshold distance.

5. The imaging modality of claim 1, wherein the imaging modality is a computed tomography system or magnetic resonance scanner.

6. The imaging modality of claim 1, wherein the at least one processor is configured to execute the computer-readable instructions to
determine a position of the mobile control element; and
determine whether the mobile control element is located greater than the first threshold distance away from the imaging modality based on the position of the mobile control element.

7. The imaging modality of claim 6, further comprising:
at least one camera, wherein
the at least one processor is configured to execute the computer-readable instructions to determine the position of the mobile control element based on information from the at least one camera.

8. The imaging modality of claim 6, wherein the at least one processor is configured to execute the computer-readable instructions to determine the position of the mobile control element based on information from at least one navigation facility.

9. The imaging modality of claim 6, wherein the at least one processor is configured to execute the computer-readable instructions to determine the position of the mobile control element according to a pulse range method based on information from at least one transmitter-receiver combination.

10. The imaging modality of claim 6, wherein the at least one processor is configured to execute the computer-readable instructions to determine the position of the mobile control element based on information from at least one GPS receiver.

11. The imaging modality of claim 1, wherein the mobile control element includes a movable trolley or a tablet PC.

12. The imaging modality of claim 1, wherein the at least one processor is configured to execute the computer-readable instructions to
   determine whether the mobile control element is located less than a second threshold distance away from the imaging modality, the second threshold distance being less than the first threshold distance, and
   disable the one or more functions of the imaging modality in response to determining that the mobile control element is located less than the second threshold distance away from the imaging modality.

13. An imaging modality comprising:
   a memory storing computer-readable instructions; and
   at least one processor coupled to the memory and configured to execute the computer-readable instructions to
      determine whether a mobile control element configured to control the imaging modality is located less than a first threshold distance away from the imaging modality and greater than a second threshold distance away from the imaging modality, the second threshold distance being less than the first threshold distance, and
      enable one or more functions of the imaging modality in response to determining that the mobile control element is located less than the first threshold distance away from the imaging modality and greater than the second threshold distance away from the imaging modality, wherein
      the imaging modality is configured to communicate with the mobile control element via a wireless communication link, and
      the first threshold distance is less than a communication range of the wireless communication link.

14. The imaging modality of claim 13, further comprising:
   an emergency shutdown switch, wherein
   the first threshold distance and the second threshold distance are measured from the emergency shutdown switch.

15. The imaging modality of claim 13, further comprising:
   a couch, wherein
   the first threshold distance and the second threshold distance are measured from the couch.

16. The imaging modality of claim 13, further comprising:
   at least one induction loop defining the first threshold distance and the second threshold distance.

17. The imaging modality of claim 13, wherein the imaging modality is a computed tomography system or magnetic resonance scanner.

18. The imaging modality of claim 13, wherein the at least one processor is configured to execute the computer-readable instructions to
   determine a position of the mobile control element; and
   determine whether the mobile control element is located less than the first threshold distance away from the imaging modality and greater than the second threshold distance away from the imaging modality based on the position of the mobile control element.

19. The imaging modality of claim 18, further comprising:
   at least one camera, wherein
   the at least one processor is configured to execute the computer-readable instructions to determine the position of the mobile control element based on information from the at least one camera.

20. The imaging modality of claim 18, wherein the at least one processor is configured to execute the computer-readable instructions to determine the position of the mobile control element based on information from at least one navigation facility.

21. The imaging modality of claim 18, wherein the at least one processor is configured to execute the computer-readable instructions to determine the position of the mobile control element according to a pulse range method based on information from at least one transmitter-receiver combination.

22. The imaging modality of claim 18, wherein the at least one processor is configured to execute the computer-readable instructions to determine the position of the mobile control element based on information from at least one GPS receiver.

23. The imaging modality of claim 13, wherein the mobile control element includes a movable trolley or a tablet PC.

24. The imaging modality of claim 13, wherein the at least one processor is configured to execute the computer-readable instructions to enable the one or more functions of the imaging modality only in response to determining that the mobile control element is located less than the first threshold distance away from the imaging modality and greater than the second threshold distance away from the imaging modality.

* * * * *